(12) United States Patent
Eller et al.

(10) Patent No.: US 12,090,038 B2
(45) Date of Patent: Sep. 17, 2024

(54) ESOPHAGEAL STENTS AND RELATED METHODS

(71) Applicant: Merit Medical Systems, Inc., South Jordan, UT (US)

(72) Inventors: Zeke Eller, Plano, TX (US); Tiffany Ethridge, Lubbock, TX (US); Bryan K. Elwood, Arlington, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 398 days.

(21) Appl. No.: 17/383,221

(22) Filed: Jul. 22, 2021

(65) Prior Publication Data

US 2022/0023026 A1 Jan. 27, 2022

Related U.S. Application Data

(60) Provisional application No. 63/056,471, filed on Jul. 24, 2020.

(51) Int. Cl.
*A61F 2/04* (2013.01)
*A61F 2/00* (2006.01)

(52) U.S. Cl.
CPC ........ *A61F 2/04* (2013.01); *A61F 2002/0081* (2013.01); *A61F 2002/044* (2013.01); *A61F 2230/0069* (2013.01); *A61F 2250/0039* (2013.01)

(58) Field of Classification Search
CPC ........... A61F 2/04–2002/048; A61F 2002/077; A61F 2002/0081; A61F 2230/0069; A61F 2250/0039; A61F 2002/8486; A61F 2/0077; A61F 2220/0008; A61F 2/82–2/97

See application file for complete search history.

(56) References Cited

U.S. PATENT DOCUMENTS

| | | | |
|---|---|---|---|
| 4,913,141 A | 4/1990 | Hillstead | |
| 5,201,757 A | 4/1993 | Heyn et al. | |
| 5,413,575 A | 5/1995 | Haenggi | |
| 5,534,007 A | 7/1996 | Germain et al. | |
| 5,591,172 A | 1/1997 | Bachmann et al. | |
| 5,591,196 A | 1/1997 | Marin et al. | |
| 5,603,698 A | 2/1997 | Roberts et al. | |

(Continued)

FOREIGN PATENT DOCUMENTS

| | | |
|---|---|---|
| CN | 210185778 | 3/2020 |
| DE | 4323866 | 1/1994 |

(Continued)

OTHER PUBLICATIONS

European Examination Report dated Feb. 18, 2015 for EP09791142.4.

(Continued)

*Primary Examiner* — Brian A Dukert
*Assistant Examiner* — Rebecca Lynee Zimmerman
(74) *Attorney, Agent, or Firm* — Dorsey & Whitney LLP

(57) ABSTRACT

Stents are disclosed herein. The stents described herein can comprise a hollow cylindrical body in which a middle region extends to a first end and also extends to an opposing second end. The first end and the second end can each comprise a plurality of flanges, within which the flanges can have either similar or different characteristics, particularly physical profiles.

19 Claims, 8 Drawing Sheets

(56) References Cited

U.S. PATENT DOCUMENTS

| | | |
|---|---|---|
| 5,645,559 A | 7/1997 | Hachtman et al. |
| 5,733,325 A | 3/1998 | Robinson et al. |
| 5,755,769 A | 5/1998 | Richard et al. |
| 5,759,186 A | 6/1998 | Bachmann et al. |
| 5,824,041 A | 10/1998 | Lenker et al. |
| 5,868,755 A | 2/1999 | Kanner et al. |
| 5,876,448 A | 3/1999 | Thompson et al. |
| 5,916,147 A | 6/1999 | Boury |
| 5,944,727 A | 8/1999 | Ahari et al. |
| 5,968,052 A | 10/1999 | Sullivan, III et al. |
| 6,015,429 A | 1/2000 | Lau et al. |
| 6,093,194 A | 7/2000 | Mikus et al. |
| 6,123,715 A | 9/2000 | Amplatz |
| 6,143,021 A | 11/2000 | Staehle |
| 6,146,415 A | 11/2000 | Fitz |
| 6,162,231 A | 12/2000 | Mikus et al. |
| 6,241,757 B1 | 6/2001 | An et al. |
| 6,270,524 B1 | 8/2001 | Kim |
| 6,283,992 B1 | 9/2001 | Hankh et al. |
| 6,368,339 B1 | 4/2002 | Amplatz |
| 6,383,211 B1 | 5/2002 | Staehle |
| 6,391,051 B2 | 5/2002 | Sullivan, III et al. |
| 6,413,269 B1 | 7/2002 | Bui et al. |
| 6,416,545 B1 | 7/2002 | Mikus et al. |
| 6,428,566 B1 | 8/2002 | Holt |
| 6,443,980 B1 | 9/2002 | Wang et al. |
| 6,447,531 B1 | 9/2002 | Amplatz |
| 6,514,261 B1 | 2/2003 | Randall et al. |
| 6,520,983 B1 | 2/2003 | Colgan et al. |
| 6,530,933 B1 | 3/2003 | Yeung et al. |
| 6,599,296 B1 | 7/2003 | Gillick et al. |
| 6,599,308 B2 | 7/2003 | Amplatz |
| 6,613,079 B1 | 9/2003 | Wolinsky et al. |
| 6,616,675 B1 | 9/2003 | Evard et al. |
| 6,629,981 B2 | 10/2003 | Dennis et al. |
| 6,645,143 B2 | 11/2003 | VanTassel et al. |
| 6,669,719 B2 | 12/2003 | Wallace et al. |
| 6,726,712 B1 | 4/2004 | Raeder-Devens et al. |
| 6,746,480 B2 | 6/2004 | Scholz et al. |
| 6,770,101 B2 | 8/2004 | Desmond, III et al. |
| 6,776,791 B1 | 8/2004 | Jody et al. |
| 6,821,295 B1 | 11/2004 | Farrar |
| 6,866,669 B2 | 3/2005 | Buzzard et al. |
| 6,893,413 B2 | 5/2005 | Martin |
| 6,926,732 B2 | 8/2005 | Derus et al. |
| 6,955,685 B2 | 10/2005 | Escamilla et al. |
| 7,004,966 B2 | 2/2006 | Edwin et al. |
| 7,083,640 B2 | 8/2006 | Lombardi et al. |
| 7,309,350 B2 | 12/2007 | Landreville et al. |
| 7,309,351 B2 | 12/2007 | Escamilla et al. |
| 7,335,224 B2 | 2/2008 | Ohlenschaeger |
| 7,393,357 B2 | 7/2008 | Stelter et al. |
| 7,473,271 B2 | 1/2009 | Gunderson |
| 7,591,848 B2 | 9/2009 | Allen |
| 7,637,942 B2 | 12/2009 | Mangiardi et al. |
| 7,731,654 B2 | 6/2010 | Mangiardi et al. |
| 7,959,671 B2 | 6/2011 | Mangiardi et al. |
| 8,012,194 B2 | 9/2011 | Edwin et al. |
| 8,206,436 B2 | 6/2012 | Mangiardi et al. |
| 8,262,719 B2 | 9/2012 | Erickson et al. |
| 8,357,193 B2 | 1/2013 | Phan et al. |
| 8,414,635 B2 | 4/2013 | Hyodoh et al. |
| 8,425,539 B2 | 4/2013 | Binmoeller et al. |
| 8,439,934 B2 | 5/2013 | Satasiya et al. |
| 8,454,632 B2 | 6/2013 | Binmoeller et al. |
| 8,518,099 B2 | 8/2013 | Chanduszko et al. |
| 8,524,132 B2 | 9/2013 | Von Oepen et al. |
| 8,535,366 B2 | 9/2013 | Mangiardi et al. |
| 8,652,099 B2 | 2/2014 | Fierens et al. |
| 8,677,874 B2 | 3/2014 | Lilburn et al. |
| 8,696,611 B2 | 4/2014 | Yaacov et al. |
| 8,715,334 B2 | 5/2014 | Clerc et al. |
| 8,834,558 B2 | 9/2014 | Nissl |
| 8,906,081 B2 | 12/2014 | Cully et al. |
| 8,926,683 B2 | 1/2015 | Darla et al. |
| 9,107,741 B2 | 8/2015 | Bui et al. |
| 9,155,643 B2 | 10/2015 | Clerc et al. |
| 9,192,496 B2 | 11/2015 | Robinson |
| 9,259,336 B2 | 2/2016 | Schaeffer et al. |
| 9,284,637 B2 | 3/2016 | Boyle et al. |
| 9,381,041 B2 | 7/2016 | Brown et al. |
| 10,285,834 B2 | 5/2019 | Cindrich et al. |
| 2001/0037141 A1 | 11/2001 | Yee et al. |
| 2002/0138095 A1 | 9/2002 | Mazzocchi et al. |
| 2002/0151967 A1 | 10/2002 | Mikus et al. |
| 2002/0183827 A1 | 12/2002 | Derus et al. |
| 2002/0193749 A1 | 12/2002 | Olovson |
| 2003/0023268 A1 | 1/2003 | Lizardi |
| 2003/0028236 A1 | 2/2003 | Gillick |
| 2003/0050686 A1 | 3/2003 | Raeder-Devens et al. |
| 2003/0135265 A1 | 7/2003 | Stinson |
| 2003/0135268 A1 | 7/2003 | Desai |
| 2003/0144671 A1 | 7/2003 | Brooks et al. |
| 2003/0167060 A1 | 9/2003 | Buzzard et al. |
| 2004/0030381 A1 | 2/2004 | Shu |
| 2004/0098077 A1 | 5/2004 | Gianotti |
| 2004/0127973 A1 | 7/2004 | Mangiardi et al. |
| 2004/0181239 A1 | 9/2004 | Dorn et al. |
| 2004/0193243 A1 | 9/2004 | Mangiardi et al. |
| 2004/0267281 A1 | 12/2004 | Harari et al. |
| 2005/0027345 A1 | 2/2005 | Horan et al. |
| 2005/0038495 A1 | 2/2005 | Greenan |
| 2005/0090887 A1 | 4/2005 | Pryor |
| 2005/0125050 A1 | 6/2005 | Carter et al. |
| 2005/0149160 A1 | 7/2005 | McFerran |
| 2005/0182475 A1 | 8/2005 | Jen et al. |
| 2005/0182481 A1 | 8/2005 | Schlick et al. |
| 2005/0278010 A1 | 12/2005 | Richardson |
| 2005/0283179 A1 | 12/2005 | Lentz |
| 2006/0020321 A1 | 1/2006 | Parker |
| 2006/0155368 A1 | 7/2006 | Shin |
| 2006/0184224 A1 | 8/2006 | Angel |
| 2006/0258972 A1 | 11/2006 | Mangiardi et al. |
| 2006/0259113 A1 | 11/2006 | Nissl |
| 2007/0005122 A1 | 1/2007 | Inoue |
| 2007/0043421 A1 | 2/2007 | Mangiardi et al. |
| 2007/0100421 A1 | 5/2007 | Griffin |
| 2007/0135904 A1 | 6/2007 | Eidenschink et al. |
| 2007/0156225 A1 | 7/2007 | George et al. |
| 2007/0179590 A1 | 8/2007 | Lu et al. |
| 2007/0208350 A1 | 9/2007 | Gunderson |
| 2007/0250150 A1 | 10/2007 | Pal et al. |
| 2007/0270932 A1 | 11/2007 | Headley et al. |
| 2008/0114443 A1 | 5/2008 | Mitchell et al. |
| 2008/0140178 A1 | 6/2008 | Rasmussen et al. |
| 2008/0228256 A1 | 9/2008 | Erickson et al. |
| 2008/0288042 A1 | 11/2008 | Purdy et al. |
| 2009/0099636 A1 | 4/2009 | Chanduszko et al. |
| 2009/0099647 A1 | 4/2009 | Glimsdale et al. |
| 2009/0118740 A1 | 5/2009 | Mangiardi et al. |
| 2009/0157158 A1 | 6/2009 | Ondracek |
| 2009/0171427 A1 | 7/2009 | Melsheimer et al. |
| 2009/0171433 A1 | 7/2009 | Melsheimer |
| 2009/0187240 A1 | 7/2009 | Clerc |
| 2009/0192518 A1 | 7/2009 | Golden et al. |
| 2009/0292262 A1 | 11/2009 | Adams et al. |
| 2010/0023032 A1 | 1/2010 | Granja et al. |
| 2010/0023132 A1 | 1/2010 | Imran |
| 2010/0030256 A1 | 2/2010 | Dubrul et al. |
| 2010/0030321 A1 | 2/2010 | Mach |
| 2010/0049295 A1 | 2/2010 | Satasiya et al. |
| 2010/0057145 A1 | 3/2010 | Bhatnagar et al. |
| 2010/0057185 A1 | 3/2010 | Melsheimer et al. |
| 2010/0070016 A1 | 3/2010 | Dorn |
| 2010/0145431 A1 | 6/2010 | Wu et al. |
| 2010/0252470 A1 | 10/2010 | Ryan et al. |
| 2011/0004290 A1 | 1/2011 | Bales, Jr. et al. |
| 2011/0015616 A1 | 1/2011 | Straubinger et al. |
| 2011/0082464 A1 | 4/2011 | Douk et al. |
| 2011/0137396 A1 | 6/2011 | Dorn et al. |
| 2011/0137400 A1 | 6/2011 | Dorn et al. |
| 2011/0190862 A1 | 8/2011 | Bashiri et al. |
| 2011/0208296 A1 | 8/2011 | Duffy et al. |
| 2011/0264191 A1 | 10/2011 | Rothstein |

(56) References Cited

U.S. PATENT DOCUMENTS

| | | |
|---|---|---|
| 2011/0288482 A1 | 11/2011 | Farrell et al. |
| 2011/0307070 A1 | 12/2011 | Clerc et al. |
| 2011/0319980 A1 | 12/2011 | Ryan |
| 2012/0046729 A1 | 2/2012 | Von Oepen et al. |
| 2012/0095567 A1 | 4/2012 | Weisman et al. |
| 2012/0136426 A1 | 5/2012 | Phan et al. |
| 2012/0290066 A1 | 11/2012 | Nabulsi et al. |
| 2012/0296257 A1 | 11/2012 | Van et al. |
| 2012/0303109 A1 | 11/2012 | Okuma |
| 2012/0303112 A1 | 11/2012 | Armstrong et al. |
| 2012/0310320 A1 | 12/2012 | Gill et al. |
| 2013/0018215 A1 | 1/2013 | Snider et al. |
| 2013/0103163 A1 | 4/2013 | Krimsky et al. |
| 2013/0110221 A1 | 5/2013 | Campbell et al. |
| 2013/0116770 A1 | 5/2013 | Robinson |
| 2013/0116771 A1 | 5/2013 | Robinson |
| 2013/0116772 A1 | 5/2013 | Robinson et al. |
| 2013/0158673 A1 | 6/2013 | Toomey |
| 2013/0184833 A1 | 7/2013 | Ryan et al. |
| 2013/0197623 A1 | 8/2013 | McHugo |
| 2013/0231689 A1 | 9/2013 | Binmoeller et al. |
| 2013/0253546 A1 | 9/2013 | Sander et al. |
| 2013/0274870 A1 | 10/2013 | Lombardi et al. |
| 2013/0310833 A1 | 11/2013 | Brown et al. |
| 2014/0074065 A1 | 3/2014 | Muni et al. |
| 2014/0074219 A1 | 3/2014 | Hingston et al. |
| 2014/0171863 A1 | 6/2014 | Blacker |
| 2014/0236064 A1 | 8/2014 | Binmoeller et al. |
| 2014/0243992 A1 | 8/2014 | Walsh et al. |
| 2014/0277573 A1 | 9/2014 | Gill et al. |
| 2014/0288636 A1 | 9/2014 | Headley, Jr. et al. |
| 2014/0303709 A1 | 10/2014 | Dwork |
| 2014/0330305 A1 | 11/2014 | Rood et al. |
| 2014/0350694 A1 | 11/2014 | Behan |
| 2014/0364959 A1 | 12/2014 | Attar et al. |
| 2015/0066128 A1 | 3/2015 | Losordo et al. |
| 2015/0100133 A1 | 4/2015 | Xie et al. |
| 2015/0112377 A1 | 4/2015 | Arnone et al. |
| 2015/0173919 A1 | 6/2015 | Baldwin |
| 2015/0230955 A1 | 8/2015 | Farag Eells et al. |
| 2015/0313595 A1 | 11/2015 | Houshton et al. |
| 2015/0313599 A1 | 11/2015 | Johnson et al. |
| 2016/0081823 A1 | 3/2016 | Majercak |
| 2016/0081832 A1 | 3/2016 | Hingston et al. |
| 2016/0242846 A1 | 8/2016 | Brown et al. |
| 2016/0256306 A1 | 9/2016 | Cindrich et al. |
| 2017/0014133 A1 | 1/2017 | Han et al. |
| 2017/0035424 A1 | 2/2017 | Binmoeller et al. |
| 2017/0035426 A1 | 2/2017 | Phan et al. |
| 2017/0035427 A1 | 2/2017 | Sander et al. |
| 2017/0035428 A1 | 2/2017 | Binmoeller et al. |
| 2017/0354404 A1 | 12/2017 | Chu |
| 2018/0185183 A1 | 7/2018 | Christakis et al. |
| 2018/0193175 A1 | 7/2018 | Bluecher et al. |
| 2018/0263797 A1 | 9/2018 | Eller et al. |
| 2018/0280166 A1 | 10/2018 | Walsh et al. |
| 2018/0303594 A1 | 10/2018 | Eller et al. |
| 2018/0338846 A1 | 11/2018 | Folan et al. |
| 2019/0099589 A1 | 4/2019 | Walsh et al. |
| 2019/0254804 A1* | 8/2019 | Folan ............... A61B 17/1114 |
| 2020/0375768 A1 | 12/2020 | Eller et al. |
| 2021/0121306 A1* | 4/2021 | Henchie ............. A61F 2/0077 |
| 2021/0145563 A1* | 5/2021 | Folan ................ A61F 2/04 |
| 2021/0161692 A1 | 6/2021 | Mower et al. |
| 2022/0125608 A1 | 4/2022 | Ethridge et al. |
| 2023/0381000 A1 | 11/2023 | Eller et al. |

FOREIGN PATENT DOCUMENTS

| | | |
|---|---|---|
| DE | 102005051469 | 4/2007 |
| EP | 0364420 | 4/1990 |
| EP | 0408245 | 1/1991 |
| EP | 0872220 | 10/1998 |
| EP | 1637092 | 3/2006 |
| EP | 2522316 | 11/2012 |
| WO | 199631174 | 10/1996 |
| WO | 200018330 | 4/2000 |
| WO | 2000078246 | 12/2000 |
| WO | 2002056798 | 7/2002 |
| WO | 2002087470 | 11/2002 |
| WO | 2003090644 | 11/2003 |
| WO | 2004030571 | 4/2004 |
| WO | 2005070095 | 8/2005 |
| WO | 2008042266 | 4/2008 |
| WO | 2010130297 | 11/2010 |
| WO | 2013045262 | 4/2013 |
| WO | 2013052528 | 4/2013 |
| WO | 2013066883 | 10/2013 |
| WO | 2015184154 | 12/2015 |
| WO | 2019099080 | 5/2019 |
| WO | 2020146261 | 7/2020 |
| WO | 2022093710 A1 | 5/2022 |

OTHER PUBLICATIONS

European Examination Report dated Apr. 26, 2021 for EP11846358.7.
European Search Report dated Mar. 19, 2021 for EP18768455.0.
European Search Report dated Apr. 24, 2020 for EP17857414.1.
European Search Report dated Nov. 9, 2020 for EP18767753.9.
European Search Report dated Dec. 15, 2020 for EP18768455.0.
European Search Reported Sep. 24, 2018 for EP16759580.
International Preliminary Report dated May 15, 2014 for PCT/US2012/062603.
International Publication and Search Report Jun. 14, 2012 for WO2012078794.
International Publication and Search Report dated Feb. 25, 2012 for WO2010021836.
International Publication and Search Report dated Aug. 4, 2005 for WO2005070095.
International Search Report and Written Opinion dated Jan. 9, 2018 for PCT/US2017/054000.
International Search Report and Written Opinion dated Mar. 16, 2012 for PCT/US2011/063799.
International Search Report and Written Opinion dated Mar. 29, 2013 for PCT/US2012/062603.
International Search Report and Written Opinion dated Jun. 22, 2016 for PCT/US2016/020900.
International Search Report and Written Opinion dated Jun. 29, 2018 for PCT/US2018/022340.
International Search Report and Written Opinion dated Jun. 29, 2018 for PCT/US2018/022344.
International Search Report and Written Opinion dated Aug. 2, 2018 for PCT/US2018/028107.
International Search Report and Written Opinion dated Sep. 28, 2005 for PCT/US2005/000515.
International Search Report and Written Opinion dated Oct. 29, 2009 for PCT/US2009/052691.
International Search Report and Written Opinion dated Nov. 23, 2006 for PCT/US2006/018811.
Notice of Allowance dated Jan. 14, 2015 for U.S. Appl. No. 11/432,964.
Notice of Allowance dated Feb. 25, 2019 for U.S. Appl. No. 15/061,107.
Notice of Allowance dated Mar. 6, 2013 for U.S. Appl. No. 12/535,980.
Notice of Allowance dated Jun. 11, 2013 for U.S. Appl. No. 10/585,430.
Notice of Allowance dated Jul. 22, 2020 for U.S. Appl. No. 15/718,419.
Notice of Allowance dated Aug. 12, 2015 for U.S. Appl. No. 13/664,200.
Notice of Allowance dated Sep. 6, 2018 for U.S. Appl. No. 29/597,873.
Notice of Allowance dated Mar. 15, 2023 for U.S. Appl. No. 16/994,260.
European Examination Report dated Feb. 2, 2023 for EP18768455.0.

(56) References Cited

OTHER PUBLICATIONS

International Search Report and Written Opinion dated Feb. 14, 2022 for PCT/US2021/056495.
International Search Report and Written Opinion dated Nov. 9, 2021 for PCT/US2021/042833.
Office Action dated Apr. 15, 2022 for U.S. Appl. No. 15/921,220.
Office Action dated Nov. 9, 2021 for U.S. Appl. No. 15/921,221.
Office Action dated Nov. 25, 2022 for U.S. Appl. No. 16/994,260.
Office Action dated Sep. 14, 2023 for U.S. Appl. No. 17/509,749.
Notice of Allowance dated Jun. 22, 2016 for U.S. Appl. No. 13/664,267.
Notice of Allowance dated Sep. 23, 2016 for U.S. Appl. No. 13/664,234.
Notice of Allowance dated Oct. 21, 2014 for U.S. Appl. No. 13/313,929.
Office Action dated Jan. 3, 2014 for U.S. Appl. No. 11/432,964.
Office Action dated Jan. 22, 2013 for U.S. Appl. No. 10/585,430.
Office Action dated Jan. 31, 2012 for U.S. Appl. No. 10/585,430.
Office Action dated Feb. 5, 2020 for U.S. Appl. No. 15/921,172.
Office Action dated Mar. 6, 2020 for U.S. Appl. No. 15/955,895.
Office Action dated Mar. 16, 2015 for U.S. Appl. No. 13/664,234.
Office Action dated Mar. 22, 2016 for U.S. Appl. No. 13/664,234.
Office Action dated Mar. 24, 2015 for U.S. Appl. No. 13/664,267.
Office Action dated Apr. 6, 2016 for U.S. Appl. No. 13/664,137.
Office Action dated Apr. 7, 2020 for U.S. Appl. No. 15/955,895.
Office Action dated Apr. 25, 2018 for U.S. Appl. No. 15/061,107.
Office Action dated May 5, 2014 for U.S. Appl. No. 13/313,929.
Office Action dated May 21, 2021 for U.S. Appl. No. 15/921,220.
Office Action dated May 25, 2012 for U.S. Appl. No. 12/535,980.
Office Action dated May 30, 2019 for U.S. Appl. No. 15/263,741.
Office Action dated Jun. 7, 2011 for U.S. Appl. No. 10/585,430.
Office Action dated Jul. 9, 2009 for U.S. Appl. No. 11/432,964.
Office Action dated Jul. 25, 2013 for U.S. Appl. No. 11/432,964.
Office Action dated Aug. 13, 2012 for U.S. Appl. No. 10/585,430.
Office Action dated Sep. 19, 2018 for U.S. Appl. No. 15/061,107.
Office Action dated Oct. 7, 2015 for U.S. Appl. No. 13/664,234.
Office Action dated Oct. 16, 2015 for U.S. Appl. No. 13/664,267.
Office Action dated Oct. 16, 2017 for U.S. Appl. No. 15/061,107.
Office Action dated Nov. 9, 2010 for U.S. Appl. No. 10/585,430.
Office Action dated Nov. 14, 2012 for U.S. Appl. No. 12/535,980.
Office Action dated Nov. 14, 2018 for U.S. Appl. No. 15/263,741.
Office Action dated Nov. 19, 2015 for U.S. Appl. No. 13/664,137.
Office Action dated Nov. 30, 2016 for U.S. Appl. No. 13/664,137.
Office Action dated Dec. 2, 2019 for U.S. Appl. No. 15/718,419.
Office Action dated Dec. 7, 2009 for U.S. Appl. No. 11/432,964.
Office Action dated Dec. 8, 2009 for U.S. Appl. No. 10/585,430.
Office Action dated Dec. 22, 2020 for U.S. Appl. No. 15/921,220.
Cheon, et al., Clinical Feasibility of a New Through-The-Scope Fully Covered Esophageal Self-Expandable Metallic Stent: An In Vivo Animal Study, Digestive Endoscopy, vol. 26 No. 1 ,2014 ,32-36.
Kawakami, et al., Endoscopic Ultrasound-Guided Transluminal Drainage for Peripancreatic Fluid Collections: Where are we now?, Gut and Liver, vol. 8 No. 4 ,2014 ,341-355.
Sen, et al., Laplace's Equation for Convective Scalar Transport in Potential Flow, Proc. R. Soc. Lond. A 456, pp. 3041-3045 ,2000.
Sizarov, et al., Novel materials and Devices in the Transcatheter Creation of vascular Anastomosis—The Future Comes Slowly (Part 2), Archives of Cardiovascular Diseases, vol. 109 No. 4 ,2016 ,286-295.
Weilert, et al., Specially Designed Stents for Translumenal Drainage, Gastrointestinal Intervention, vol. 4 No. 1 ,2015,40-45.
Notice of Allowance dated Jan. 8, 2024 for U.S. Appl. No. 17/509,749.
European Search Report dated Jul. 5, 2024 for EP21847135.7.

\* cited by examiner

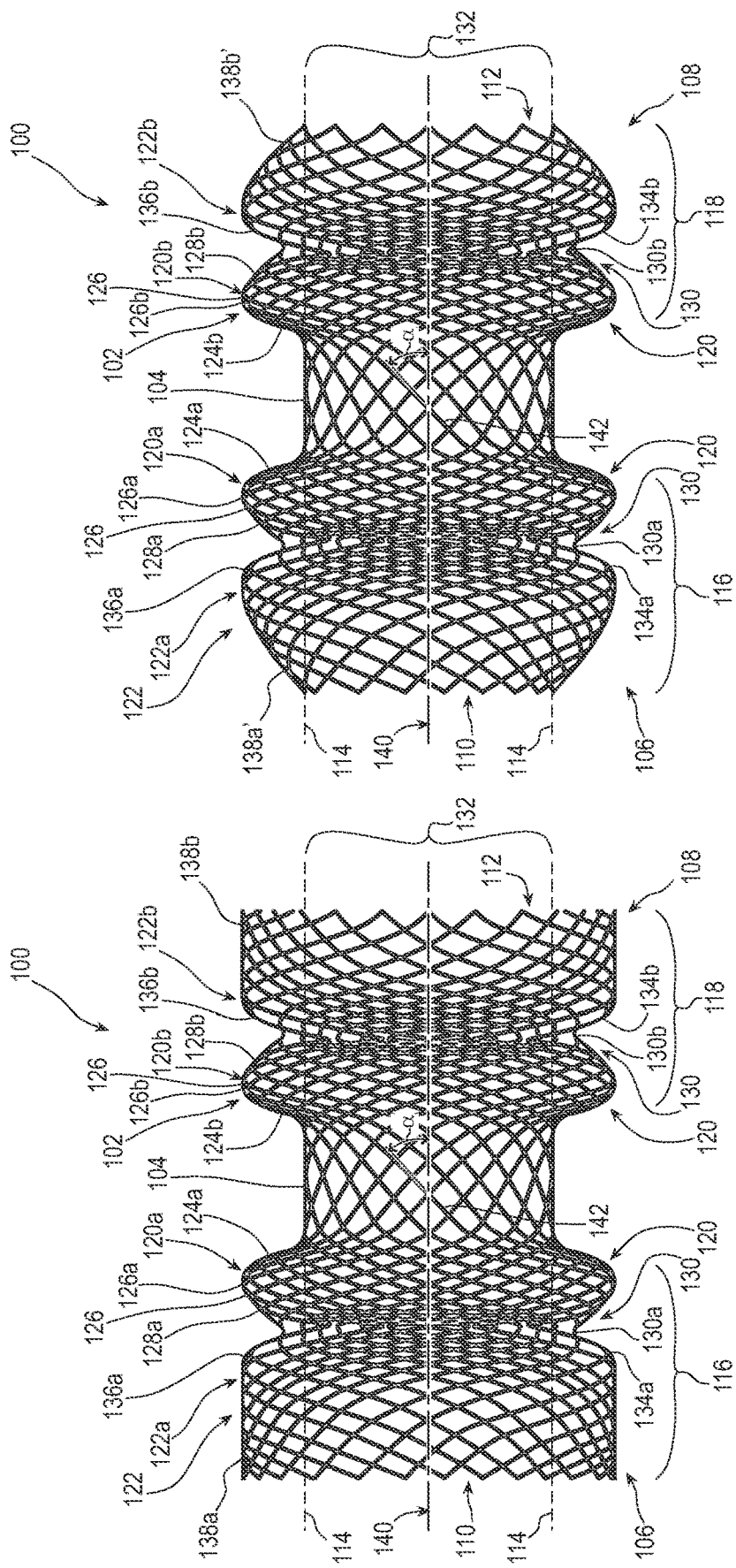

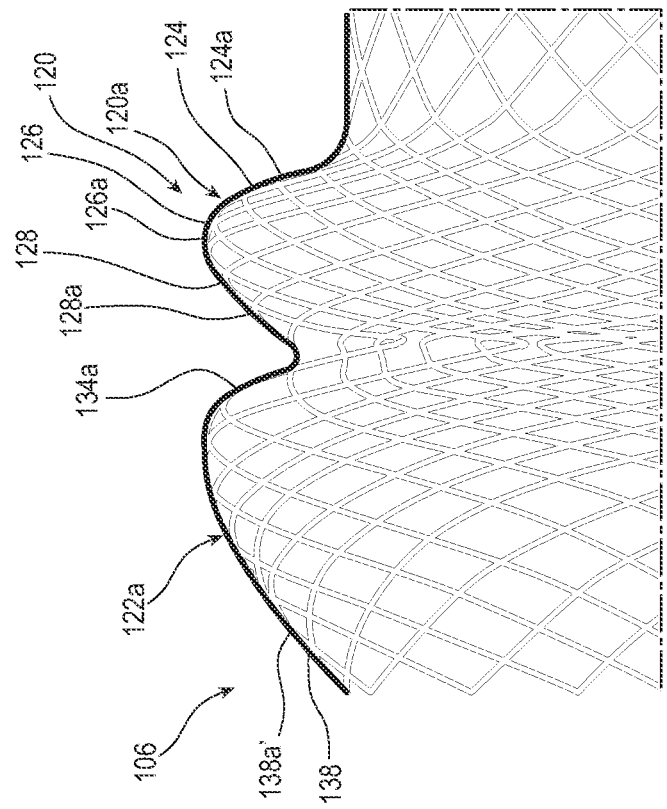
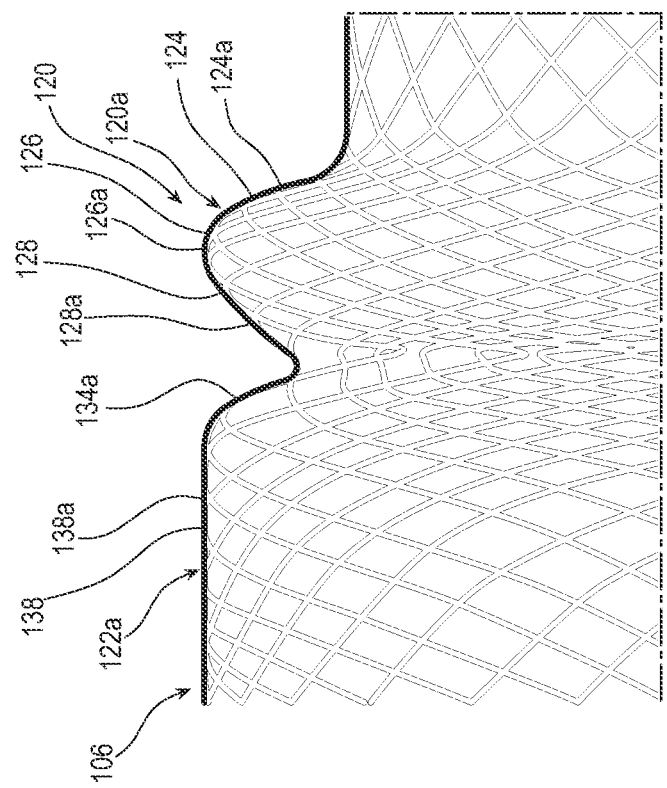
FIG. 2A
FIG. 2B

ESOPHAGEAL STENTS AND RELATED METHODS

RELATED APPLICATIONS

This application claims priority to U.S. Provisional Application No. 63/056,471, filed Jul. 24, 2020, and titled ESOPHAGEAL STENTS AND RELATED METHODS, which is incorporated herein by reference in its entirety.

TECHNICAL FIELD

This application generally relates to medical devices. More particularly, this application relates to esophageal stents and related methods.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A shows a side view of an exemplary embodiment of a stent in an unelongated and unstretched state.

FIG. 1B shows a side view illustrating an alternative aspect of the exemplary embodiment shown in FIG. 1A.

FIG. 2A shows a longitudinal cross-section of a portion of the embodiment shown in FIG. 1A.

FIG. 2B shows a longitudinal cross-section of a portion of the embodiment shown in FIG. 1B.

DETAILED DESCRIPTION

Figure 3:
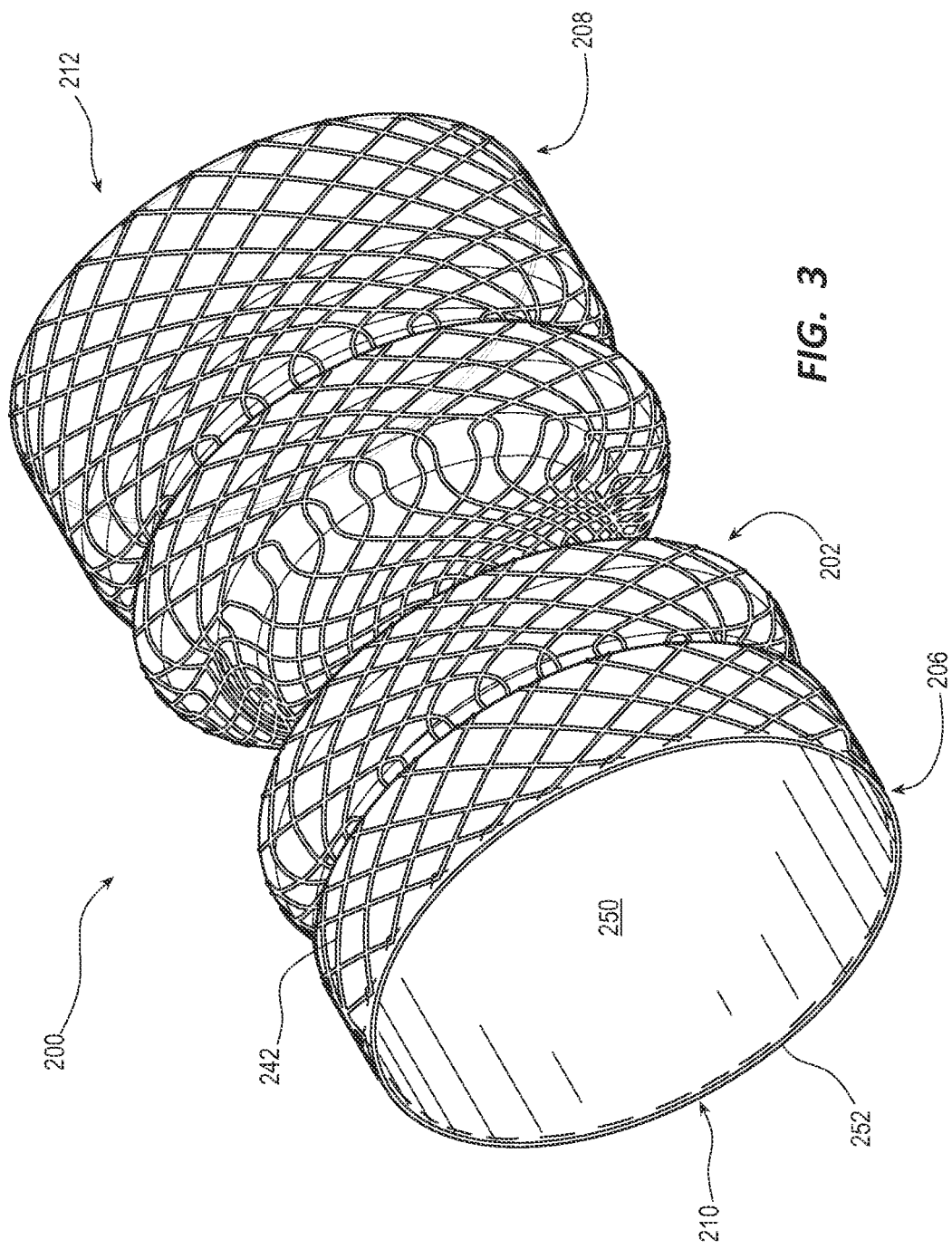
FIG. 3 shows a perspective view of another embodiment of a stent.

Stents are disclosed herein. In some embodiments, the stents described herein comprise a hollow cylindrical body having an interior dimension and comprising a middle region that extends to a first end and also extends to an opposing second end. The interior dimension refers to the three-dimensional space within the stent. As used herein, the hollow cylindrical body may refer to generally cylindrical shapes and forms, including stents with flared ends, for example. The first end and the second end can each comprise a plurality of flanges, within which the flanges can have either similar or different characteristics, particularly physical profiles.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As applied a stent deployed within an esophagus, the proximal end of the stent refers to the end closest to the patient's head, and the distal end of the stent refers to the opposite end, the end closer to the patient's stomach.

FIGS. 1A and 1B illustrate exemplary embodiments of a stent in an unelongated and unstretched state. The stent 100 comprises a hollow cylindrical body 102. The hollow cylindrical body 102 comprises a middle region 104 that extends to a first end 106 and also extends to an opposing second end 108. Two openings provide access to the interior of the hollow cylindrical body 102: a first opening 110 defined by the first end 106 and a second opening 112 defined by the second end 108.

In an aspect, one end of the stent body will be the proximal end and the other will be the distal end as defined herein. In some embodiments, the stent is configured so that either the first end or the second end can be proximal with the remaining end being distal based on the practitioner's choice. In other embodiments, use of the stent indicates that a specific end is consistently designated as the proximal end. In such embodiments described herein, the first end is intended for designation as the proximal end and the second end is intended for designation as the distal end unless expressly indicated otherwise.

In the illustrated embodiments, each of the ends comprises a plurality of flanges, flares, or flared regions that extend radially from the circumference 114 of the middle region 104. However, it should be noted that embodiments in which only one end includes these and other features described herein are also encompassed by the present disclosure. These flanges are configured to interact with the surfaces of a lumen in the body of a subject into which the stent 100 is deployed (e.g., such as the esophagus). More specifically, the first end 106 comprises a first plurality of flanges 116 and the second end 108 comprises a second plurality of flanges 118. As shown, each of the first plurality and the second plurality include at least two flanges. More specifically, the first plurality of flanges 116 includes an inner flange 120a adjacent to the middle region 104 and an outer flange 122a adjacent to the first opening 110, and the second plurality of flanges 118 similarly includes an inner flange 120b adjacent to the opposing end of the middle region 104 and an outer flange 122b adjacent to the second opening 112. As used herein in discussing the shapes and arrangement of flanges, "inner" refers to the side facing or in the direction of the middle region, while "outer" refers to the side facing or in the direction of the nearest opening. Additionally, while the embodiments shown herein depict a plurality of flanges on each end, it will also be appreciated that in some embodiments only one end of the stent includes a plurality of flanges, while the opposing end includes a singular flange.

FIGS. 1A and 1B also illustrate shapes for the flanges in accordance with various embodiments. In this and in subsequent figures, multiple occurrences of an element are indicated with a series of suffixes "a", "b", etc., added to a base reference number. Discussion herein of such an element that references its base reference number (e.g. 120) is understood to apply similarly to all occurrences (e.g. 120a, 120b) unless otherwise indicated. Likewise, relationships between two or more such elements (e.g., 120, 122) are understood to apply between occurrences indicated by the same suffix (e.g. 120a, 122a).

As shown in FIGS. 1A and 1B, the inner flange in each plurality can have a profile that is roughly triangular so as to form a hump-like structure protruding from the circumference of the middle region. In the embodiments shown, the profile of each of the inner flange 120 comprises an inner shoulder 124 extending radially from the circumference 114 to a peak 126 and an outer taper 128 returning from the peak 126 back toward the longitudinal axis 140 to a valley 130. In some embodiments, the diameter of the inner flange 120 at the peak 126 is at least about 2 mm greater than the diameter of the middle region 104. In more particular embodiments, the diameter of the inner flange 120 at the peak 126 is from about 2 mm greater to about 15 mm greater than the diameter of the middle region 104, or more particularly from about 3 mm to about 12 mm. In some embodiments, the diameter of the inner flange 120 at the peak 126 is between about 1.2 times and about 2.5 times the diameter of the middle region 110. In a particular aspect, the valley 130 defines an inner diameter that is at least equal to the diameter 132 of the middle region 104. In some embodiments, the inner diameter of the valley 130 can be somewhat or slightly larger than that of the middle region 104. For example, the diameter of the valley 130 can be between about 1.0 times and about 1.5 times larger than the diameter of the middle region 104.

As noted above, the outer flange 122 defines the adjacent opening into the interior of the stent. The profile of the outer flange 122 comprises an inner shoulder 134 extending from the circumference 114 or valley 130 to a peak 136. In some embodiments, the peak 136 of the outer flange 122 is the same height relative to the circumference 114 as the peak 126 of the inner flange 120. In certain embodiments, as exemplified by FIG. 1A, the outer flange 122 further comprises a cylindrical outer section 138 that is both concentric to the longitudinal axis 140 of the hollow cylindrical body 102 and parallel to the circumference 114, and that extends to the adjacent opening. In other embodiments as exemplified in FIG. 1B, the profile of the outer flange 122 is similar to that of the inner flange 120 in that the outer section 138 tapers toward the longitudinal axis 140 to define the adjacent opening.

In some embodiments, the overall length of the stent may range from about 30 mm to about 250 mm, including ranging from about 30 mm to about 70 mm or from about 160 mm to about 250 mm. In some embodiments, the length of the first end and/or the second end (which can include the plurality of flanges) in the unelongated and unstretched state may each range from about 10 mm to about 30 mm, including ranging from about 14 mm to about 22 mm. In some embodiments, the length of the middle region may range from about 5 mm to about 210 mm, including ranging from about 10 mm to about 30 mm and from about 30 mm to about 120 mm and from about 120 mm to about 210 mm. Smaller and/or larger stents are also contemplated depending on the desired use. For example, in some embodiments, the stents are configured for deployment within the esophagus. However, the disclosure is not so limited and other types of stents are also contemplated, including, but not limited to, gastrointestinal stents (including colonic stents), biliary stents, lung stents, vascular stents, transluminal stents, pancreatic stents, etc.

As shown in FIG. 1, the hollow cylindrical body 102 may comprise braided or woven wire 142. More specifically, the wires can be arranged in a particular braid pattern having a pitch, and with a braid angle $\alpha$ that can be constant over a given region of the body and also vary over other regions to provide certain shape and strength characteristics. In some embodiments, the braid pattern of the middle region 104 (and of the entire stent 100) is a one-wire, two-over, two-under braid pattern (referred to as a "one over two" pattern), which means that a single strand passes over two strands (or two different portions of itself, such as in a single wire braid design) and then under two other strands (or yet two other portions of itself, such as in a single wire braid design). Alternative braid patterns may be used as well, such as a one-wire, one-over, one-under braid pattern (referred to as a "one over one" pattern). Other possible braid patterns include the diamond two-wire, one-over, one-under braid pattern and the diamond two, two-over, two-under braid pattern.

In some embodiments, the braid pattern may lead to differing cell requirements over the length of the stent 100, where a cell refers to the design created by the braid pattern. Thus, depending on stent length and braid pattern, the braid designs may result in fractional and non-fractional cell counts. For example, a stent may be designed with a non-fractional cell count, in which a full braid pattern is completed on each end of the stent and/or the stent comprises only full braid patterns along the length of the stent. Non-fractional cell counts refer to a whole cell count. For example, a stent with a non-fractional cell count may have, 20, 30, 40, 50, or more full cell counts, or full braid patterns along its length. Fractional cell counts refer to fractional cell count numbers, 20.5, 30.5, 40.5, 50.5 or more, meaning the stent has a whole number of full cell counts in addition to a partial cell (or braid pattern) along the length of the stent. In some embodiments, the braid pattern may be one over one and may have a fractional or non-fractional cell count. In some embodiments, the braid pattern may be one over two and may have a fractional or non-fractional cell count.

As shown in FIGS. 1A and 1B, the braid angle $\alpha$ is an angle formed by a given strand of the braided or woven wire 142 relative to the longitudinal axis 140 of the stent 100. A larger (higher) braid angle, approaching, for example, 90 degrees, results in a higher pic count (number of points of intersection of the strands) per given longitudinal length (e.g., an inch) of a given braid (or weave) pattern. These parameters can be varied to impart certain characteristics to the stent body. A higher pic count can produce greater stiffness (i.e., a lower degree of compressibility). A smaller (lower) braid angle results in a lower pic count per given longitudinal length, which can result in greater softness (i.e., less stiffness and a higher degree of compressibility). In some embodiments, the braid angle α is from about 35° to about 75°, or more particularly from about 40° to about 70°. In certain of such embodiments, the braid angle α in the middle region is between about 35° and about 60°, and the braid angle α at the peaks of the flanges is between about 60° and about 70°. In some embodiments, the braid angle α is substantially constant over the middle region. In some embodiments, the braid angle α is substantially uniform at a peak of a flange while varying uniformly over the inner shoulder and the outer taper.

The pitch (i.e., axial distance between crossing strands) also impacts the compressibility and stiffness of the braided or woven wires. In an aspect, a sufficiently tight pitch can impart better migration resistance to the stent. The pitch is related to the number of strands interwoven (or interbraided) with each other and the braid angle α, and therefore can vary over different geometries. In some embodiments, the pitch is substantially constant over the middle region. In some embodiments, the pitch is substantially uniform at a peak of a flange while varying uniformly over the inner shoulder and the outer taper.

The braided or woven wires may be braided or woven in a given pattern in accordance with an appropriate braid design, such as a closed-loop braid design, a single wire woven design, an endless braid design, or the like. In some embodiments, the wire is braided in a closed-loop braid design in which multiple strands are interlaced in a first direction (e.g., a distal direction) and then turn and are interlaced back in an opposite second direction (e.g., back in the proximal direction). In still other embodiments, the stent may have an endless braid design in which multiple strands are interlaced. In some embodiments, the braid pattern can comprise hook stitches. In other embodiments, a "hook and cross" braid pattern is used in which the pattern includes both hook stitches and cross stitches. In some embodiments, the braid pattern is created using an axial braiding approach. In some embodiments, the braid pattern is created using a radial braiding approach. Radial braiding involves creating a fractional cell count along the length of the stent, either a non-fractional or a fractional cell count can be selected with axial braiding.

In various embodiments, the braided or woven wires are braided or woven so as to create a series of loops at one or both ends of the stent. The arrangement of these loops can be selected to provide desired functionality, such as for threading through of a suture line (discussed further below). In some embodiments the end loops are substantially aligned in one plane at the stent opening (see e.g., FIGS. 1A and 1B). In other embodiments, some end loops may protrude further than others. In certain embodiments, the position of the end loops can alternate (see e.g. FIG. 7).

The braided or woven wires may include varying numbers of strands, where the number used can depend in part upon the size of the stent and the braid or weave pattern. In some embodiments, the stent includes a wire count of from 32 to 64 wires, or more particularly from 45 to 50 wires, or more particularly from 48-56 wires.

When braided or woven in a closed-loop braid design, the braided or woven wires may start and stop at various locations on the stent 100. In an aspect, it can be advantageous to design the braid so that such termination points occur on surfaces that include a substantially flat dimension. In some embodiments, at least one wire termination point is on the middle region of the stent. In certain embodiments, such as the embodiment illustrated in FIG. 1A, at least one wire termination point is on the cylindrical outer section of an outer flange.

In various embodiments, the braided or woven wires forming the stent may comprise any suitable material known in the art, including plastics and memory alloys. In some embodiments, the wires may be Nitinol, including ASTM F2063. In certain embodiments, the thickness of a memory alloy strand of the braided or woven wires may be about 140 µm to about 191 µm. In other embodiments, the thickness may be about 165 µm to about 178 µm. Generally speaking, smaller wires may be used with smaller diameter stents and larger diameter wires may be used with larger diameter stents. Also, while smaller diameter wires can be used for stents designed for "through-the-scope" placement, stents designed for "over the wire" placement can include wires having significantly larger diameters. Radiopaque markers and/or coils can also be incorporated into the stent as desired.

Additional aspects of the flanges in the embodiments described above are illustrated in FIGS. 2A and 2B, each of which show a cross-section of a portion of the first end 106 of one of the embodiments shown in FIGS. 1A and 1B, said portion defined by bisecting the hollow cylindrical body 102 both vertically and horizontally along the longitudinal axis 140. In some embodiments, an aspect of the inner shoulders of the various flanges is that they extend from the circumference 114 at an angle, slope, or arc that can be substantially perpendicular. An aspect of the inner flange 120 in particular is that the inner shoulder 124 includes a region that is substantially perpendicular to the longitudinal axis 140 while the outer taper 128 does not include such a perpendicular region. Another way to characterize the profile of the inner flange 120 is that the profile is asymmetric and includes a compound curve in which the different sections of the flange surface feature curves having different orientations and radii. In the illustrated embodiments, for example, the inner shoulder 124 includes a curve that is oriented more perpendicularly than a curve included in the outer taper 128, while the peak 126 includes a substantially horizontal curve having a smaller radius than the other curves. The profile of the inner flange 120 can also be described as an arc of an ellipse that is tilted inward from perpendicular, resulting in a hump having different slopes on its inner and outer faces. In yet further embodiments, the inner shoulder 124 can be described as extending outward at a steeper or more inclined angle, slope, or arc as compared to the outer taper 128 that extends inwards at a less steep or inclined angle, slope, or arc relative to the longitudinal axis of the stent.

The perpendicularly oriented region (or more perpendicularly oriented region having a steeper or more inclined angle, slope, or arc) of the inner shoulder 124 results in the peak 126 and, more generally the inner flange 120, exerting a hoop force against the tissue walls of a lumen in a subject so as to facilitate greater retention of the stent 100 in the body lumen. In another sense, the shape of the inner flange 120 functions as a shoulder region that resists longitudinal migration of the stent 100 due to peristalsis or other forces, in a manner that is independent of the magnitude of the hoop force. The shallower incline, angle, slope, or arc of the outer taper 128 increases stiffness of the inner flange 120 as compared to a flange that includes a perpendicular region on both inner and outer faces. For example, a flange having a symmetrical profile can tend to deflect more outwardly when in use, as compared to embodiments where the inner shoulders include more perpendicular regions, but the outer tapers do not include corresponding perpendicular regions.

The same aspects apply to each outer flange in embodiments in which said outer flange has a similar profile to that of the inner flange, such as with the outer flange 122*a* having a tapered outer section 138*a*' in the embodiment illustrated in FIG. 2B. Similar effects are also provided in other embodiments in which the outer flange comprises a cylindrical outer section, such as the embodiment illustrated in FIG. 2A. That is, the inner shoulder 134 acts to facilitate greater retention of the stent 100 by exerting a force on the lumen walls, which is further facilitated by the increased stiffness contributed by the outer section 138. The cylindrical outer section 138 can provide the additional function of forming a seal with the lumen wall, such that material moving within the lumen passes into the opening defined by the outer section and through the body of the stent, rather than bypassing the opening and potentially getting stuck between the stent body and the lumen wall. The particular design of the outer flange can result in enhanced outward force exerted on the outer section, thereby increasing the quality of the seal.

In an aspect, the magnitude and nature of these effects can vary based on physical dimensions of the outer section, such as its length and diameter. For example, attaining such performance from a stent of a particular size may involve said stent including an outer section having a minimum length. On the other hand, increasing the length of the outer section means a concomitant increase in the overall length of the stent, which in turn can be limited by the particular clinical use. In various embodiments, the length of the outer segment can be selected so as to provide sufficient retention and sealing performance while keeping the overall stent length within applicable parameters for the intended use. Another consideration is provided where the cylindrical outer section is used as a termination surface for the woven or braided wire from which the stent body is made. Accordingly, in some embodiments, the outer segment has a length equal to at least one cell of the braid pattern.

The benefits of increased stiffness and strength provided by the flange shapes described above can be enhanced by combining two or more flanges in a "stacked" configuration in accordance with the various embodiments described herein. Without being bound or limited by a particular theory, the retention forces generated by the individual flanges can increase as a function of the number of flanges arranged together. Stated another way, in a plurality of flanges, one flange can increase the resistance of an adjacent flange to deformation and vice versa, thereby increasing the capacity of both flanges to resist migration of the stent.

FIG. 3 shows another embodiment of a stent 200 including the features of the stent 100 shown in FIG. 1A, and further including a cover 250. The cover is coupled to the braided or woven wire 242 that forms the hollow cylindrical body 202. The cover 250 can further define the interior of the stent 200 and can facilitate passage of particles or fluid through the interior.

The cover may be elastomeric, polymeric, or comprised of any other material known in the art. In some embodiments, the cover may include silicone, while in certain embodiments the cover may be comprised only of silicone. In some embodiments, the cover may be applied such that it tends to ebb and flow into spaces between portions of the braided or woven wires, resulting in a "tire tread" like outer surface, rather than a smooth outer cover. This can allow tissue to lock into the uneven spaces and treads, thus adding anti-migration properties in some embodiments. In some embodiments, the cover is shaped such that the braided or woven wires are uncovered in some regions of the stent, which can allow tissue to grow into these spaces to help secure the stent in place. For instance, the peaks of the flanges can be at least partially uncovered, which can allow tissue ingrowth. In some embodiments, the cover can comprise two or more layers of material.

The stent 200 in FIG. 3 further includes a suture line 252 situated at the first end 206 of the hollow cylindrical body 202 and woven through the mesh created by the wire 242. As shown, the suture line 252 circumscribes the first opening 210. In some embodiments, the suture line 252 can be woven through end loops formed at an end of the hollow cylindrical body 202. The suture line 252 can be configured to aid with loading of the stent 200 into a catheter or other delivery device and can also facilitate removal of the stent 200 from a patient. The suture line 252 may be woven in such a way that pulling it has a drawstring effect on the first opening 210. That is, pulling a portion of the suture line 252 away from the first opening 210 causes the suture to draw the edges of the cover 250 and the first opening 210 radially inward, elongating and narrowing the hollow cylindrical body 202. In the case where the stent 200 is situated in a body lumen, this action facilitates removal by causing the stent 200 to disengage from the lumen wall. In some embodiments, a suture line can also be included at the second end 208 and can function similarly with respect to the second opening 212.

As discussed above, certain benefits can be realized in stents having two or more flanges in a stacked arrangement at each end, including an increased capacity to retain the stent's position in a lumen. Accordingly, in some embodiments a plurality of flanges can include one or more additional flanges situated between the inner flange and outer flange. For instance, one, two, three, four or more additional flanges may be disposed between the inner and outer flanges, resulting in a total of three, four, five, six, or more total flanges on an end of the stent. Further, in some embodiments, a proximal end of the stent can be configured with additional flanges (or more flanges) than the distal end to aid in preventing migration of the stent. Such an arrangement can be advantageous, although not required, when employing the stent in an esophagus.

Figure 4A:
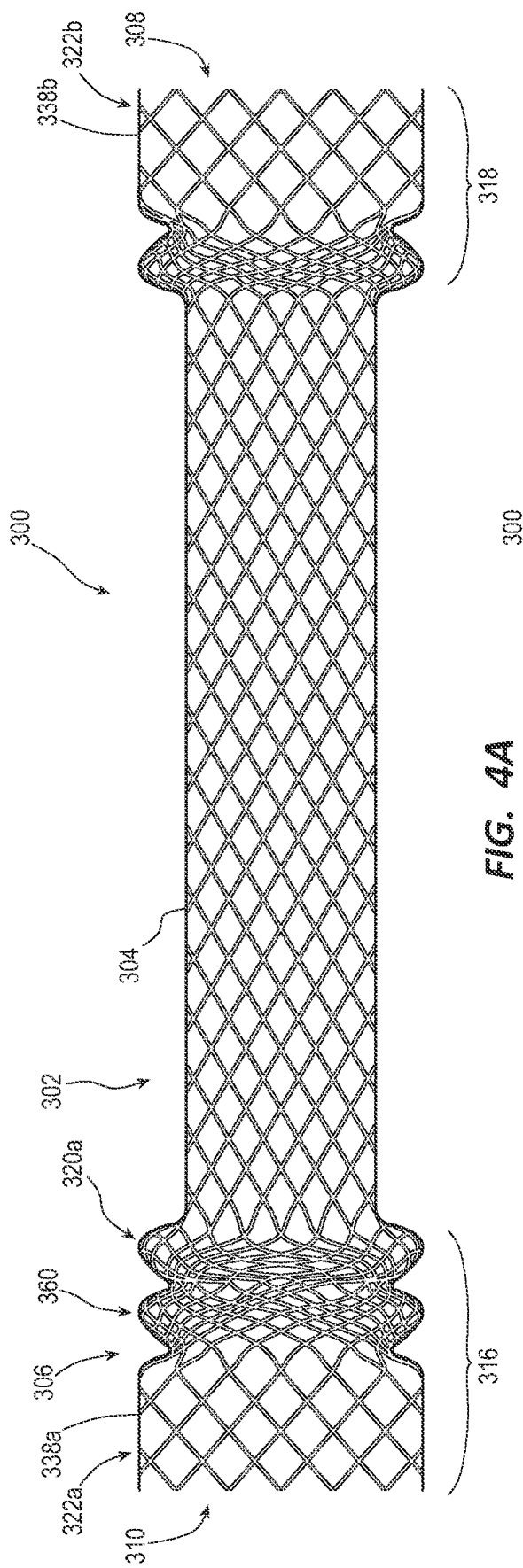
FIG. 4A shows a side view of another exemplary embodiment of a stent in an unelongated and unstretched state.
Figure 4B:
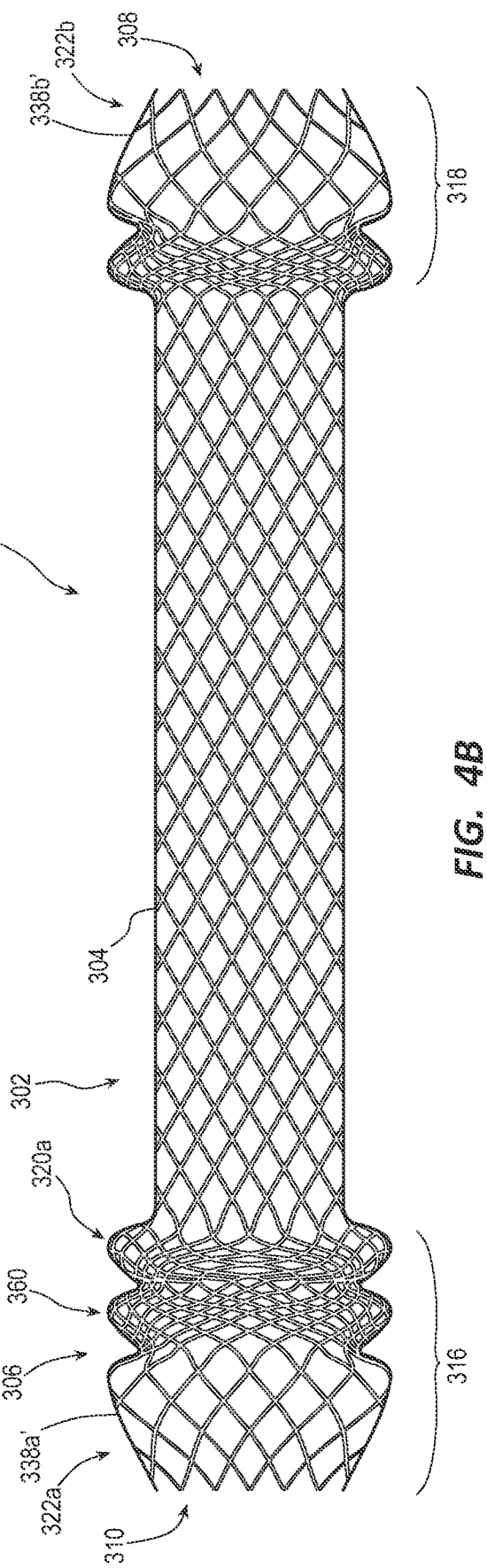
FIG. 4B shows a side view illustrating an alternative aspect of the exemplary embodiment shown in FIG. 4A.

FIGS. 4A and 4B show an example embodiment of a stent 300 in which a hollow cylindrical body 302 comprises a middle region 304 that extends to a first end 306 and also extends to an opposing second end 308, and where the first end 306 comprises a first plurality of flanges 316 and the second end 308 comprises a second plurality of flanges 318. As shown, the first plurality of flanges 316 comprises an inner flange 320*a* adjacent to the middle region 304 and an outer flange 322*a* adjacent to the first opening 310, where the outer flanges 322*a* and 322*b* can feature an outer section 338*a* and 338*b*, respectively, that is cylindrical as shown in FIG. 4A, or a tapered outer section 338*a*' and 338*b*' respectively as shown in FIG. 4B. The first plurality of flanges 316 of this embodiment further comprises an additional flange 360 situated between these two. In some embodiments, as illustrated here, the additional flange 360 has a profile that is substantially the same as the inner flange 320*a*.

Figure 5A:
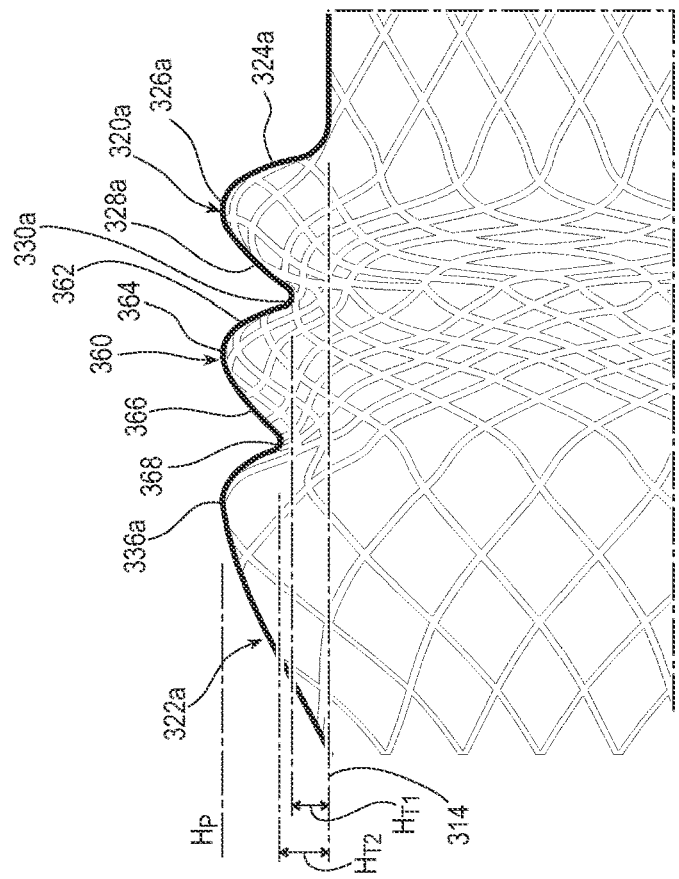
FIG. 5A shows a longitudinal cross-section of a portion of the embodiment shown in FIG. 4A.
Figure 5B:
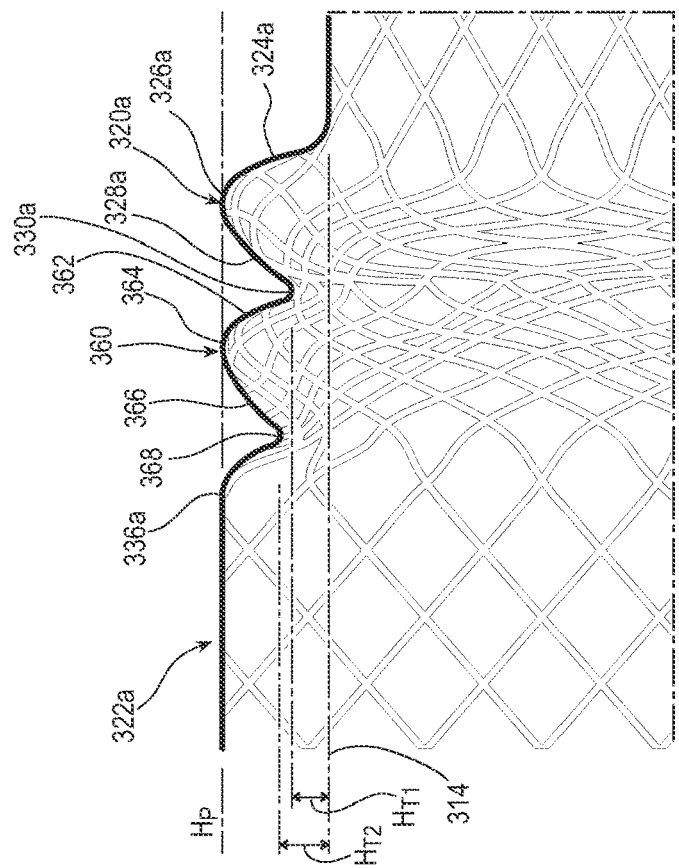
FIG. 5B shows a longitudinal cross-section of a portion of the embodiment shown in FIG. 4B.

FIGS. 5A and 5B each show a cross-section of a portion of the first end 306 of the embodiments shown in FIGS. 4A and 4B, said portion defined using the same approach as in FIGS. 2A and 2B. As shown, a plurality of flanges, particularly one comprising three or more flanges, can include selected relative spatial and dimensional characteristics. The first plurality of flanges 316 of the embodiment shown in FIGS. 4A and 4B are shown in closer detail in FIGS. 5A and 5B, respectively. As shown, the profile of inner flange 320*a* comprises an inner shoulder 324a extending radially from the circumference 314 to a peak 326a and an outer taper 328a returning from the peak 326a back toward the longitudinal axis (not visible in this view) to a valley 330a. In the embodiment, the additional flange 360 has a similar profile, comprising an inner shoulder 362 extending radially from the valley 330a to a second peak 364, and an outer taper 366 returning from the peak 364 back toward the longitudinal axis to a second valley 368. In some embodiments, all of the peaks of a plurality of flanges are substantially the same height above the circumference of the middle region. In other embodiments, the peaks in a plurality of flanges can vary in height. In some embodiments, the height of the peaks varies in a random fashion. In other embodiments, the height of the peaks varies according to a pattern, such as alternating in height. This is illustrated in FIGS. 5A and 5B, where the peak 326a of the inner flange 320a, the peak 364 of the additional flange 360, and the peak 336a of the outer flange 322a all have substantially the same height HP. In various embodiments, one or more valleys in a plurality of flanges sit at a level at least equal in height to the circumference of the middle region. Stated another way, the valleys define a part of the interior having an inner diameter substantially equal to that of the middle region. In some embodiments, the valleys can be situated above the level of the circumference of the middle region, i.e. define a diameter larger than that of the middle region. In some embodiments, the valleys can be situated below the level of the circumference of the middle region, i.e. define a diameter smaller than that of the middle region. FIGS. 5A and 5B illustrate a more particular embodiment in which the valleys become successively more shallow the more outwardly situated they are. Stated another way, each valley defines a diameter that is greater than any valleys closer to the middle region. As shown, valley 330a is situated at a height $H_{T1}$ above the circumference 314 and defines a particular inner diameter, while valley 368 is situated at height $H_{T2}$ above the circumference 314 and therefore defines a greater inner diameter.

Figure 6:
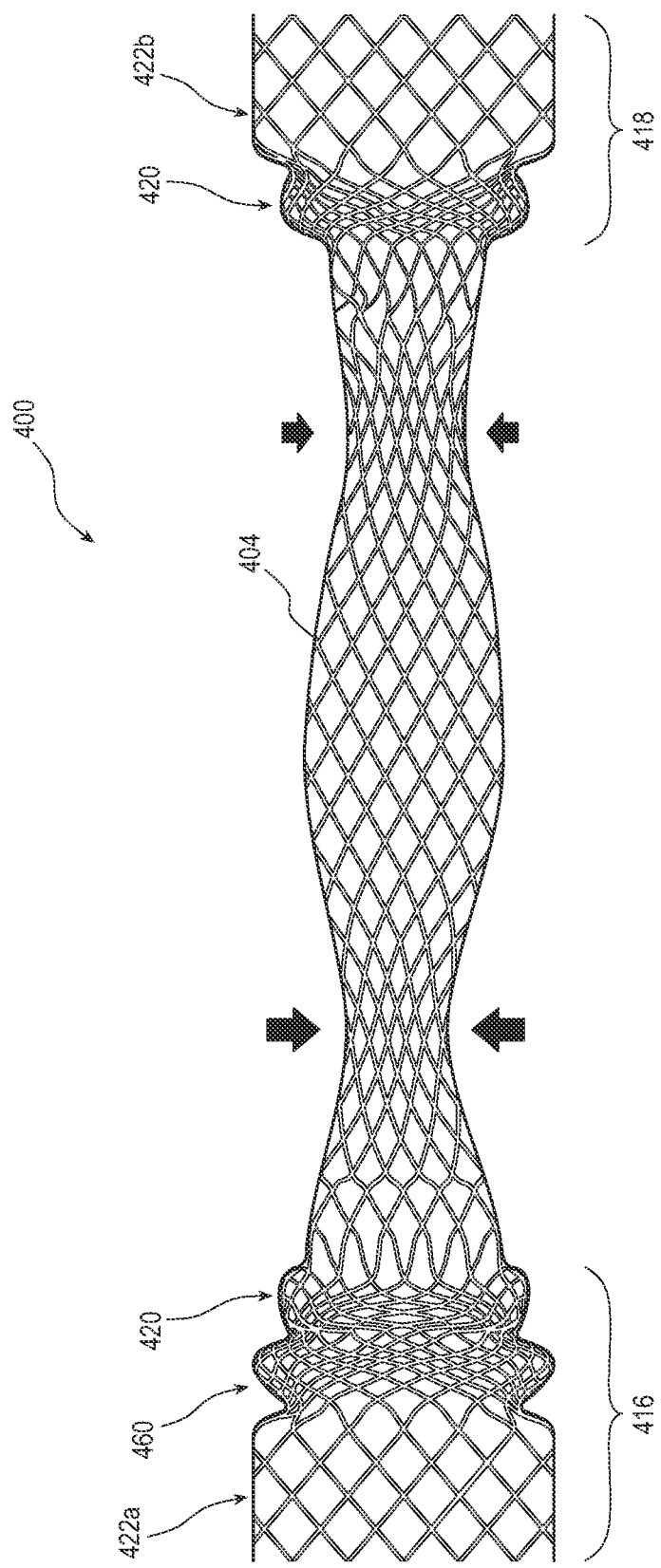
FIG. 6 illustrates an aspect of the embodiment shown in FIG. 5A.

FIG. 6 illustrates the function of stents described herein. Specifically, FIG. 6 shows a stent 400 wherein the middle region 404 is undergoing compression, such as may occur in a body lumen due to peristalsis, tumor growth, or other constrictive phenomena. Without being bound by or limited to a particular theory, one aspect of the cooperative function of stacked flanges is illustrated, where the compression at the middle region 404 is sufficient to deform each inner flange 420 but the more outward flanges (i.e. the outer flange 422a and the additional flange 460 of the first plurality of flanges 416 as well as the outer flange 422b of the second plurality of flanges 418) substantially retain their shape. It is contemplated therefore that these features allow the stent 400 to better maintain engagement with the lumen wall and resist migration within the lumen.

Figure 7:
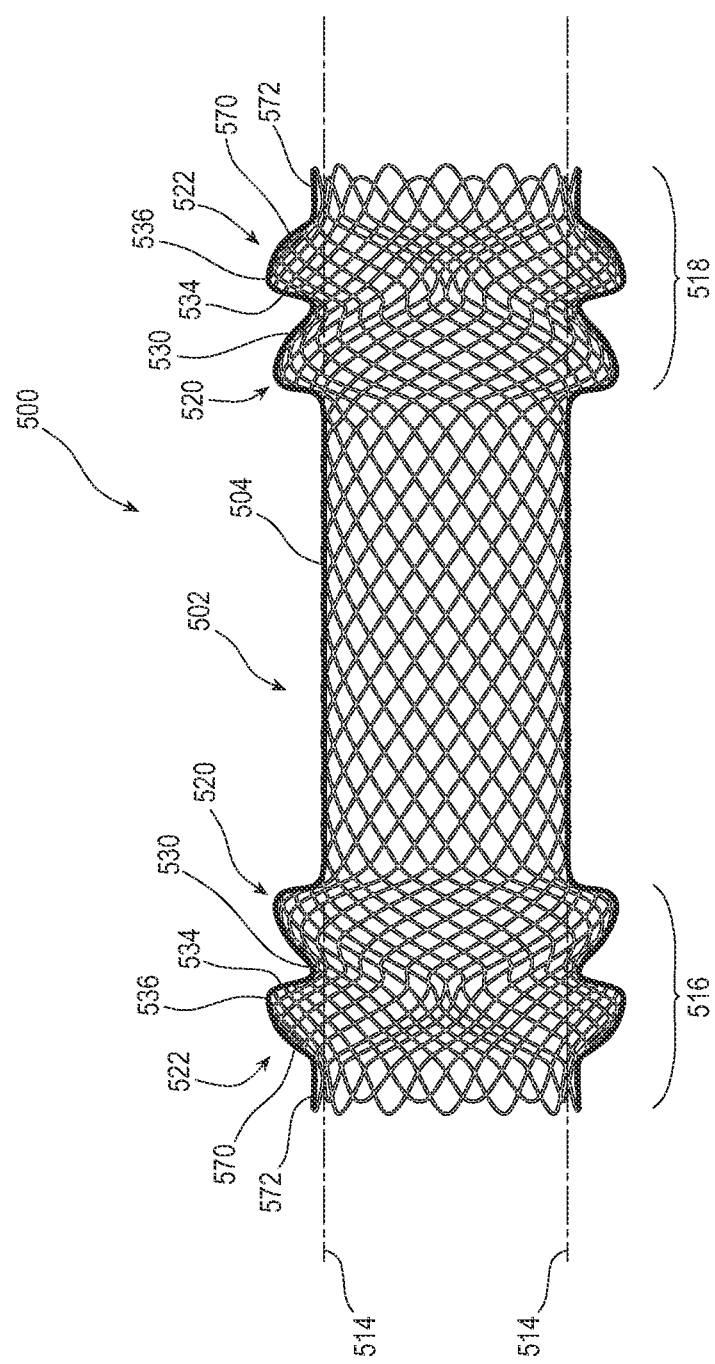
FIG. 7 illustrates a side view of another embodiment of a stent.

FIG. 7 shows another embodiment of a stent 500 in which each of the pluralities of flanges 516, 518 includes an inner flange 520 adjacent to the middle region 504 and an outer flange 522 adjacent to a corresponding end. The profile of each outer flange 522 comprises an inner shoulder 534 extending from the adjacent valley 530 to a peak 536. The outer flange 522 further comprises both an outer taper 570 and a cylindrical outer section 572, in which the outer taper 570 extends toward the longitudinal axis of the hollow cylindrical body 502 to the cylindrical outer section 572, which is both concentric to said axis and parallel to the circumference 514 of the hollow cylindrical body, and which extends to the adjacent opening. In some embodiments, the outer taper 570 meets the outer section 572 at an equal or greater height above the circumference 514 as the adjacent valley.

Figure 8:
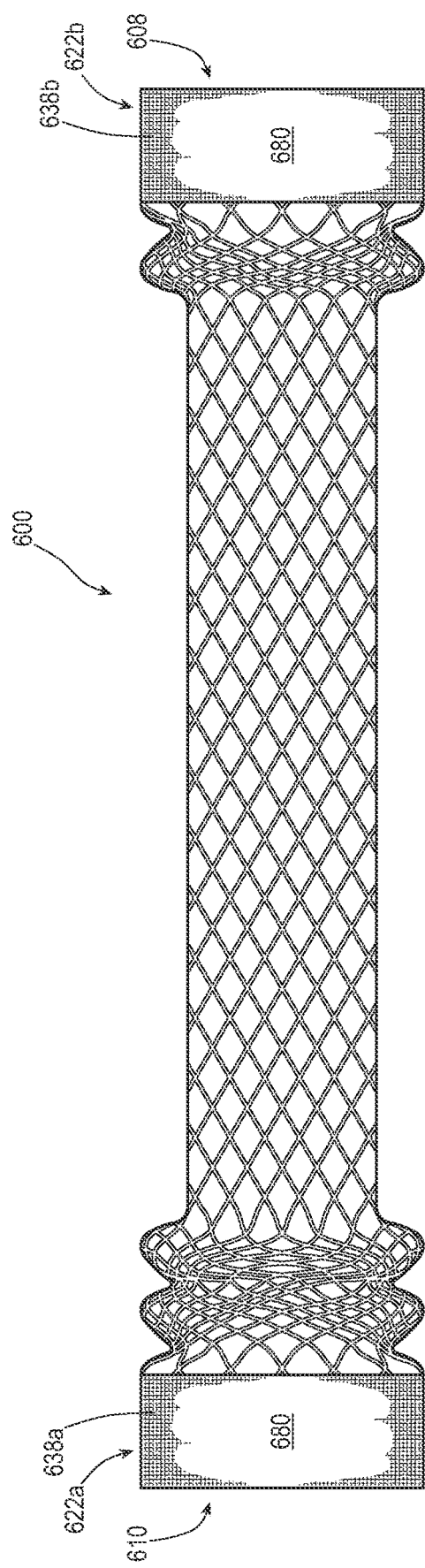
FIG. 8 illustrates a side view of another embodiment of a stent.

Stents as described above, may include additional features, including but not limited to anti-migration features, adhesives, and the like. For instance, a strip of a specialized material can be disposed on an external surface of the stent. In some embodiments, the specialized material provides a textured surface. In certain embodiments, the textured surface provides increased and/or decreased friction with surfaces into which the stent comes into contact, e.g., a tissue surface, as compared to the other regions of the outer surface of the stent body. In a particular example, the textured surface includes a multilayered/micropatterned surface in which friction is dependent on conditions in its environment, for example the wetness of the material. Examples of such materials are described in U.S. Patent Application Publication Nos. 2011/0311764 and 2017/0014111. In an aspect, such material can provide the stent with enhanced grip on surrounding tissues with less injury to said tissues. In some embodiments, a specialized material can be disposed on the external surface of the entirety of the stent, or of a designated portion thereof. For instance, as shown in the stent 600 in FIG. 8, the specialized material 680 may be disposed on a portion of one or both ends 608, 610 such as on one or both outer flanges 622a, 622b comprising a cylindrical outer section 638a, 638b.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "substantially" and "about." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration. All ranges also include both endpoints.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A stent comprising:
a hollow cylindrical body having a middle region having a circumference, a diameter, and a longitudinal axis, the middle region extending to a first end defining a first opening and comprising a first plurality of flanges and to a second end defining a second opening and comprising a second plurality of flanges,
wherein each of the first plurality of flanges and the second plurality of flanges includes at least an inner flange adjacent to the middle region and an outer flange adjacent to the corresponding opening, wherein each inner flange has a profile comprising an inner shoulder extending radially from the circumference to a peak and an outer taper returning from the peak back toward the longitudinal axis to a valley, and
wherein each valley defines a diameter that is greater than the diameter of any cross section of the middle region.

2. The stent of claim 1, wherein each outer flange has a profile that is substantially the same as the profile of each inner flange.

3. The stent of claim 1, wherein each outer flange comprises an inner shoulder extending outward from the valley to a peak and an outer section parallel and concentric to the longitudinal axis and extending from the peak to the corresponding opening.

4. The stent of claim 1, wherein at least one of the first plurality of flanges and the second plurality of flanges further includes a number of additional flanges situated between the inner flange and the outer flange, wherein said number is from 1 to 4, and wherein each of the additional flanges has a profile that is substantially the same as the profile of the inner flange.

5. The stent of claim 4, wherein the first plurality of flanges includes a number of additional flanges, and each valley in the first plurality of flanges defines a diameter that is greater than any valleys within the first plurality of flanges that are closer to the middle region.

6. The stent of claim 4, wherein the peaks in the at least one of the first plurality of flanges and second plurality of flanges vary in height above the circumference of the middle region.

7. The stent of claim 1, wherein at least a portion of the inner shoulder of the profile of each inner flange is substantially perpendicular to the longitudinal axis of the middle region.

8. The stent of claim 1, further comprising a textured surface disposed on at least a portion of the hollow cylindrical body.

9. The stent of claim 8, wherein the textured surface is a micropatterned surface.

10. The stent of claim 8, wherein the textured surface provides increased friction with respect to a tissue surface as compared to the outer surface of the tubular body.

11. A stent comprising:
a hollow cylindrical body having a middle region having a circumference, a diameter, and a longitudinal axis, the middle region extending to a first end defining a first opening and comprising a first plurality of flanges and to a second end defining a second opening and comprising a second plurality of flanges,
wherein each of the first plurality of flanges and the second plurality of flanges includes an inner flange adjacent to the middle region and an outer flange adjacent to the corresponding opening, wherein each inner flange has a profile comprising an inner shoulder extending radially from the circumference of the middle region to a peak and an outer taper returning from the peak back toward the longitudinal axis to a valley, and
wherein each valley defines a diameter that is greater than any cross-sectional diameter of the middle region, and wherein each of the first opening and second opening has a diameter at least substantially equal to an adjacent outer flange diameter.

12. The stent of claim 11, wherein in at least one of the first plurality of flanges and the second plurality of flanges, a profile of the outer flange comprises an inner shoulder extending outward from the circumference to a peak and an outer section parallel and concentric to the longitudinal axis and extending from the peak to the corresponding opening.

13. The stent of claim 11, wherein at least one of the first plurality of flanges and the second plurality of flanges further includes a number of additional flanges situated between the inner flange and the outer flange, wherein said number is from 1 to 4, and where each of the additional flanges has a profile that is substantially the same as the profile of the inner flange.

14. The stent of claim 11, wherein all of the peaks in the at least one of the first plurality of flanges and second plurality of flanges are substantially equal in height above the circumference of the middle region.

15. The stent of claim 13, wherein the first plurality of flanges includes a number of additional flanges, and each valley in the first plurality of flanges defines a diameter that is greater than any valleys within the first plurality of flanges that are closer to the middle region.

16. The stent assembly of claim 11, further comprising a textured surface disposed on at least a portion of the hollow cylindrical body.

17. The stent of claim 16, wherein the textured surface is a micropatterned surface.

18. The stent of claim 16, wherein the textured surface provides increased friction with respect to a tissue as compared to the outer surface of the tubular body.

19. A stent comprising:
a hollow cylindrical body having a middle region having a circumference, a diameter, and a longitudinal axis, the middle region extending to a first end defining a first opening and comprising a first plurality of flanges and to a second end defining a second opening and comprising a second plurality of flanges,
wherein each of the first plurality of flanges and the second plurality of flanges includes at least an inner flange adjacent to the middle region and an outer flange adjacent to the corresponding opening, wherein each inner flange has a profile comprising an inner shoulder extending radially from the circumference to a peak and an outer taper returning from the peak back toward the longitudinal axis to a valley, and wherein each of the first opening and second opening has a diameter at least substantially equal to an adjacent outer flange diameter.

\* \* \* \* \*